US00PP26139P2

(12) United States Plant Patent
Verschoor

(10) Patent No.: US PP26,139 P2
(45) Date of Patent: Nov. 24, 2015

(54) ***PHLOX* PLANT NAMED 'VERSOLDPINK'**

(50) Latin Name: *Phlox paniculata*
Varietal Denomination: Versoldpink

(71) Applicant: Janus Verschoor, Haarlem (NL)

(72) Inventor: Janus Verschoor, Haarlem (NL)

( * ) Notice: Subject to any disclaimer, the term of this patent is extended or adjusted under 35 U.S.C. 154(b) by 103 days.

(21) Appl. No.: 13/998,908

(22) Filed: Dec. 19, 2013

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Susan McCormick Ewoldt
(74) *Attorney, Agent, or Firm* — C. A. Whealy

(57) ABSTRACT

A new and distinct cultivar of *Phlox* plant named 'Versoldpink', characterized by its upright and relatively compact plant habit; freely flowering habit; large inflorescences with red purple, purple and white-colored flowers; long flowering period; good garden performance and resistance to Powdery Mildew.

2 Drawing Sheets

Botanical designation: *Phlox paniculata.*
Cultivar denomination: 'VERSOLDPINK'.

BACKGROUND OF THE INVENTION

The present invention relates to a new and distinct cultivar of *Phlox* plant, botanically known as *Phlox paniculata* and hereinafter referred to by the name 'Versoldpink'.

The new *Phlox* plant is a product of a planned breeding program conducted by the Inventor in Haarlem, The Netherlands. The objective of the breeding program was to create new compact and freely-flowering *Phlox* plants with attractive flower colors.

The new *Phlox* plant originated from a cross-pollination made by the Inventor in 2007 in Haarlem, The Netherlands, of two unnamed seedling selections of *Phlox paniculata*, not patented. The new *Phlox* plant was discovered and selected by the Inventor as a single flowering plant from within the progeny of the stated cross-pollination in a controlled environment in Haarlem, The Netherlands in 2009.

Asexual reproduction of the new *Phlox* plant by cuttings in a controlled environment in Haarlem, The Netherlands since 2009 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Versoldpink'. These characteristics in combination distinguish 'Versoldpink' as a new and distinct *Phlox* plant:

1. Upright and relatively compact plant habit.
2. Freely flowering habit.

3. Large inflorescences with red purple, purple and white-colored flowers.
4. Long flowering period.
5. Good garden performance.
6. Resistance to Powdery Mildew.

Plants of the new *Phlox* and the parent selections differ primarily in the following characteristics:

1. Plants of the new *Phlox* are shorter and more compact than plants of the parent selections.
2. Plants of the new *Phlox* and the parent selections differ in inflorescence shape.
3. Plants of the new *Phlox* are stronger and more resistant to Powdery Mildew than plants of the parent selections.

Plants of the new *Phlox* can be compared to plants of *Phlox paniculata* 'Anastasia', not patented. In side-by-side comparisons conducted in Haarlem, The Netherlands, plants of the new *Phlox* and 'Anastasia' differed in the following characteristics:

1. Plants of the new *Phlox* were shorter and more compact than plants of 'Anastasia'.
2. Plants of the new *Phlox* were more freely flowering than plants of 'Anastasia'.
3. Plants of the new *Phlox* had larger inflorescences than plants of 'Anastasia'.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Versoldpink' grown in a container.

The photograph on the second sheet is a close-up view of a typical flower of 'Versoldpink'.

DETAILED BOTANICAL DESCRIPTION

The aforementioned photographs and following observations, measurements and values describe plants grown during the late summer and early autumn in 1.5-liter containers in an outdoor nursery in Haarlem, The Netherlands and under cultural practices typical of commercial *Phlox* production. During the production of the plants, day temperatures ranged from 14° C. to 28° C. and night temperatures ranged from 6° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Phlox paniculata* 'Versoldpink'.

Parentage:

*Female, or seed, parent*.—Unnamed seedling selection of *Phlox paniculata*, not patented.

*Male, or pollen, parent*.—Unnamed seedling selection of *Phlox paniculata*, not patented.

Propagation:

*Type*.—By cuttings.

*Time to initiate roots, summer*.—About three weeks at temperatures about 20° C.

*Time to produce a rooted plant, summer*.—About six weeks at temperatures about 20° C.

*Root description*.—Fine, fibrous; white in color.

*Rooting habit*.—Moderately freely branching; medium density.

Plant description:

*Plant and growth habit*.—Herbaceous perennial; upright and relatively compact plant habit; broad inverted triangle; low vigor.

*Plant height*.—About 27.3 cm.

*Plant width* (*spread*).—About 23.3 cm.

*Lateral branches*.—Length: About 8.6 cm to 11.6 cm. Diameter: About 3 mm to 7 mm. Internode length: About 1.7 cm. Strength: Strong. Aspect: Upright to about 30° from vertical. Texture: Smooth, glabrous. Color: Close to 144A.

Leaf description:

*Arrangement*.—Opposite, simple.

*Length*.—About 8.9 cm.

*Width*.—About 2.8 cm.

*Shape*.—Ovate to elliptic, slightly carinate.

*Apex*.—Acute.

*Base*.—Truncate.

*Margin*.—Entire, revolute.

*Texture, upper and lower surfaces*.—Smooth, glabrous.

*Venation pattern*.—Pinnate.

*Color*.—Developing leaves, upper surface: Close to 143A. Developing leaves, lower surface: Close to 146C tinged with close to N199A. Fully expanded leaves, upper surface: Between N137A and 147A; venation, close to 146B. Fully expanded leaves, lower surface: Close to 147B; venation, close to 145A to 145B.

*Petioles*.—Length: About 4 mm. Diameter: About 2 mm by 4 mm. Texture, upper and lower surfaces: Smooth, glabrous. Color, upper and lower surfaces: Close to 145A.

Flower description:

*Flower type and flowering habit*.—Single rotate and salverform flowers arranged in compound terminal panicles; flowers face mostly upright to outwardly; panicles roughly pyramidal in shape; freely flowering habit with about 180 flowers developing per inflorescence.

*Fragrance*.—Moderately fragrant; sweet, pleasant. Natural flowering season: Plants begin flowering about nine months after planting; long flowering period, plants flower continuously from July through September in The Netherlands.

*Postproduction longevity*.—Flowers last about ten days on the plant; flowers not persistent.

*Flower buds*.—Height: About 2.3 cm. Diameter: About 5 mm. Shape: Narrowly elliptic to narrowly oblanceolate. Color: Close to 77B to 77D; towards the base, close to N77A; immature calyx, close to 146C to 146D and tinged with close to N77D.

*Inflorescence height*.—About 16.4 cm.

*Inflorescence diameter*.—About 15.3 cm.

*Flower diameter*.—About 3.3 cm.

*Flower depth*.—About 2.2 cm.

*Petals*.—Quantity per flower: Typically five in a single whorl; petals fused at the base into a narrow tube. Length: About 3.8 cm; lower 2.1 cm fused. Lobe width: About 2 cm. Shape: Spatulate. Apex: Rounded. Margin: Entire. Texture, upper and lower surfaces: Smooth, glabrous; slightly velvety. Color: When opening, upper surface: Close to 71B to 71D; towards the base, close to 76B to 76C; throat, between 60A and N79C. When opening, lower surface: Close to 76B to 76C and N78C to N78D; tube, between 61A and 71A. Fully opened, upper surface: Close to 72C to 72D and N78C; towards the base, close to 76D and NN155C; throat, between 60A and N79C; with development color becoming closer to N74C to N74D and 76D and the throat, close to N77A to N77B. Fully opened, lower surface: Close to 76B to 76C; tube, between 71A and N77B.

*Sepals*.—Quantity per flower: Typically five in a single whorl, fused towards the base; calyx, campanulate. Length: About 1 cm. Width: About 2 mm. Shape: Lanceolate. Apex: Narrowly apiculate. Margin: Entire. Texture, upper and lower surfaces: Smooth, glabrous. Color: When opening, upper surface: Close to 145A tinged with close to N77D. When opening, lower surface: Close to 146C to 146D tinged with close to N77D. Fully opened, upper surface: Close to 145A tinged with close to N186C. Fully opened, lower surface: Between 145A and 146D tinged with close to N186C.

*Peduncles*.—Length, primary peduncles: About 13.3 cm. Diameter, primary peduncles: About 3 mm. Length, secondary peduncles: About 3.8 cm. Diameter, secondary peduncles: About 2 mm. Aspect, primary peduncles: Erect. Aspect, secondary peduncles: About 55° from vertical. Strength: Strong. Texture: Smooth, glabrous. Color: Close to 145A.

*Pedicels*.—Length: About 5 mm. Diameter: About 1 mm. Angle: About 30° from the peduncle axis. Strength: Strong. Texture: Smooth, glabrous. Color: Close to 145A.

*Reproductive organs*.—Stamens: Quantity per flower: Typically five; filaments fused with petals. Filament length: About 1 mm. Filament color: Close to 145C. Anther length: About 2 mm. Anther shape: Oblong. Anther color: Close to 4D. Pollen amount: Moderate. Pollen color: Close to 11D. Pistils: Quantity per flower: One. Pistil length: About 1.9 cm. Stigma shape: Cleft, three-parted. Stigma color: Close to 150C. Style length: About 1.7 cm. Style color: Close to 150B. Ovary color: Close to 143A to 143B.

*Seeds and fruits*.—Seed and fruit development have not been observed on plants of the new *Phlox*.

Garden performance: Plants of the new *Phlox* have been observed to have good garden performance and tolerate rain, wind, high temperatures about 35° C. and to be winter hardy to USDA Hardiness Zone 6.

Disease & pest resistance: Plants of the new *Phlox* have been observed to be resistant to Powdery Mildew; plants of the new *Phlox* have not been observed to be resistant to pests and other pathogens common to *Phlox* plants.

It is claimed:

1. A new and distinct *Phlox* plant named 'Versoldpink' as illustrated and described.

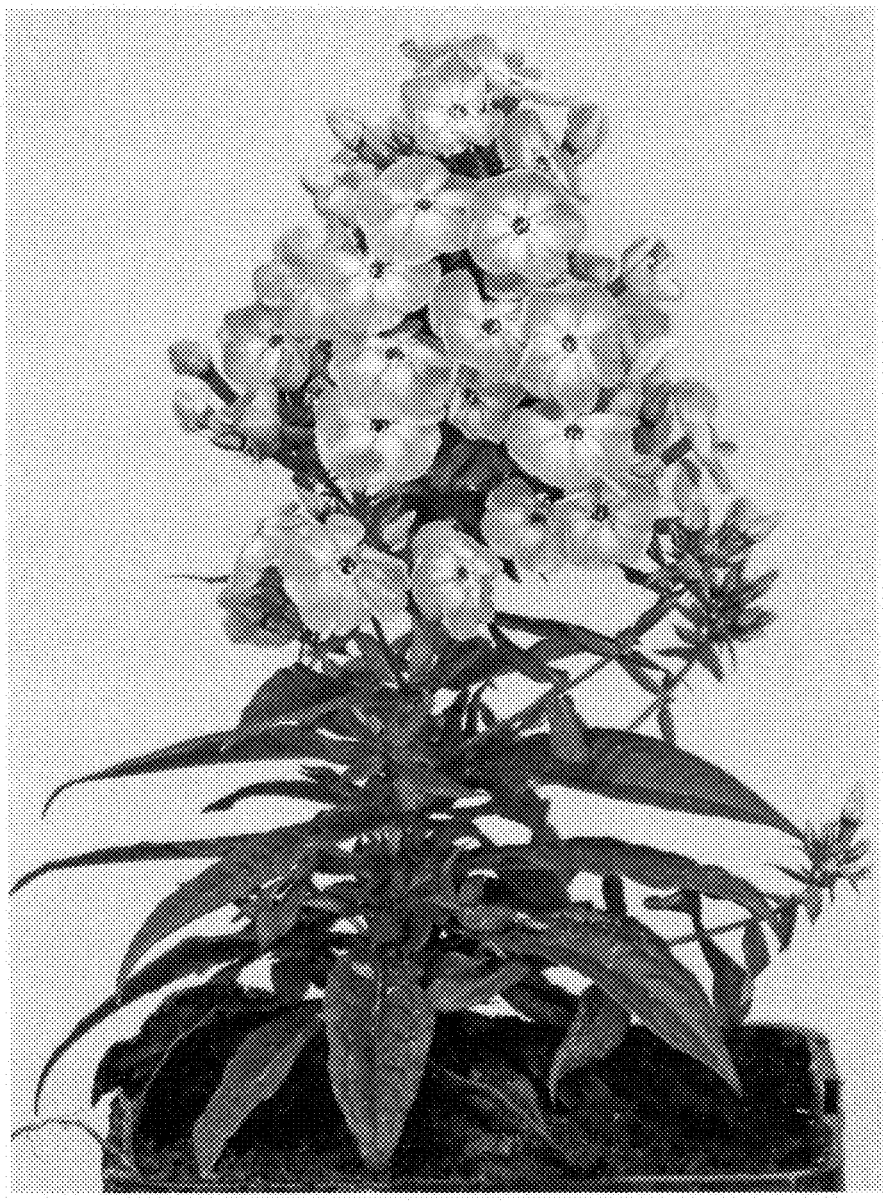

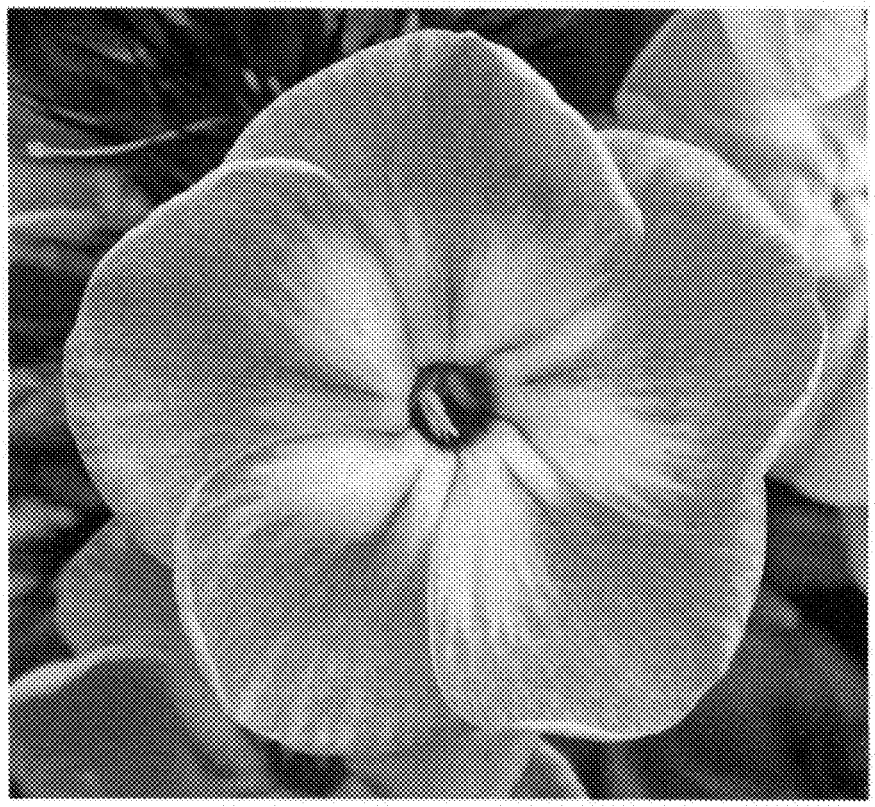

* * * * *